United States Patent
Irish et al.

(10) Patent No.: US 11,614,172 B2
(45) Date of Patent: Mar. 28, 2023

(54) PINCH VALVE

(71) Applicant: Carten Controls Limited, Waterford (IE)

(72) Inventors: Declan Irish, Waterford (IE); Shane Molloy, Waterford (IE)

(73) Assignee: Carten Controls Limited, Waterford (IE)

( * ) Notice: Subject to any disclaimer, the term of this patent is extended or adjusted under 35 U.S.C. 154(b) by 16 days.

(21) Appl. No.: 16/613,556

(22) PCT Filed: May 15, 2017

(86) PCT No.: PCT/EP2017/061643
§ 371 (c)(1),
(2) Date: Nov. 14, 2019

(87) PCT Pub. No.: WO2018/210403
PCT Pub. Date: Nov. 22, 2018

(65) Prior Publication Data
US 2021/0033204 A1 Feb. 4, 2021

(51) Int. Cl.
*F16K 7/06* (2006.01)
*F16K 7/04* (2006.01)
*A61M 39/28* (2006.01)
*F16K 31/122* (2006.01)

(52) U.S. Cl.
CPC ............ *F16K 7/061* (2013.01); *F16K 7/045* (2013.01); *A61M 39/28* (2013.01); *F16K 31/1221* (2013.01)

(58) Field of Classification Search
CPC . F16K 7/061; F16K 7/045; F16K 7/04; F16K 31/1221; F16K 31/14; F16K 27/0236; A61M 39/28
See application file for complete search history.

(56) References Cited

U.S. PATENT DOCUMENTS

| | | | |
|---|---|---|---|
| 3,412,742 A | 11/1968 | Smith | |
| 3,436,054 A | 4/1969 | Cole et al. | |
| 3,920,215 A | 11/1975 | Knauf | |
| 4,257,446 A | 3/1981 | Ray | |
| 4,259,985 A * | 4/1981 | Bergmann | F16K 7/045 137/595 |
| 4,516,593 A * | 5/1985 | Muto | F16K 43/00 251/8 |

(Continued)

FOREIGN PATENT DOCUMENTS

| | | |
|---|---|---|
| EP | 0336663 A2 | 10/1989 |
| FR | 873587 A | 7/1942 |
| GB | 693028 A | 6/1953 |

*Primary Examiner* — Mary E McManmon
*Assistant Examiner* — Andrew J Rost
(74) *Attorney, Agent, or Firm* — Kusner & Jaffe

(57) ABSTRACT

A pinch valve assembly is provided for compression of a fluid conduit comprising an assembly housing (1); an interchangeable compressor element (2); an interchangeable holder element (3) for holding a fluid conduit, the holder element facing the interchangeable compressor element; the valve assembly being configured such that the compressor element is moveable towards the holder element within the assembly housing for compression of a fluid conduit between the compressor and the holder elements.

11 Claims, 5 Drawing Sheets

(56) References Cited

U.S. PATENT DOCUMENTS

| | | | | | |
|---|---|---|---|---|---|
| 4,877,053 | A | * | 10/1989 | Yusko, Jr. | F16K 7/061 |
| | | | | | 137/556 |
| 4,895,341 | A | * | 1/1990 | Brown | F16K 7/061 |
| | | | | | 251/63.4 |
| 4,899,783 | A | * | 2/1990 | Yusko, Jr. | F16K 7/061 |
| | | | | | 137/556 |
| 5,197,708 | A | * | 3/1993 | Campau | F16K 7/061 |
| | | | | | 251/8 |
| 5,316,262 | A | * | 5/1994 | Koebler | F16K 7/061 |
| | | | | | 137/13 |
| 6,386,505 | B2 | * | 5/2002 | Schob | A61M 39/28 |
| | | | | | 251/129.07 |
| 6,755,388 | B2 | * | 6/2004 | Furukawa | F16K 7/07 |
| | | | | | 251/5 |
| 9,127,773 | B2 | * | 9/2015 | Ams | F16K 7/045 |
| 9,127,781 | B2 | * | 9/2015 | Opfer | F16K 31/143 |
| 2014/0166918 | A1 | * | 6/2014 | Kropf | F16K 7/126 |
| | | | | | 251/331 |

* cited by examiner

Figures

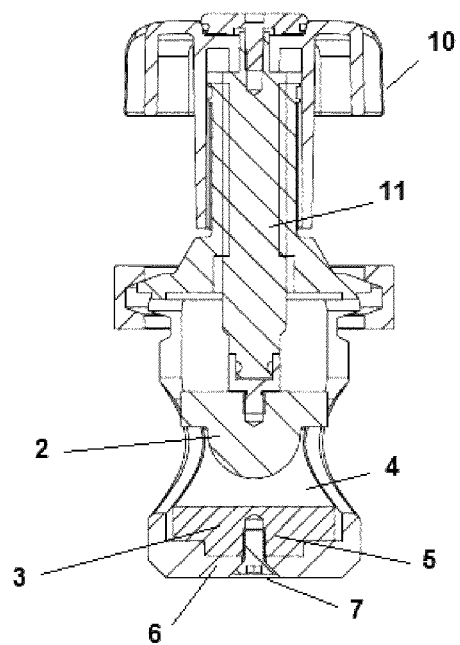
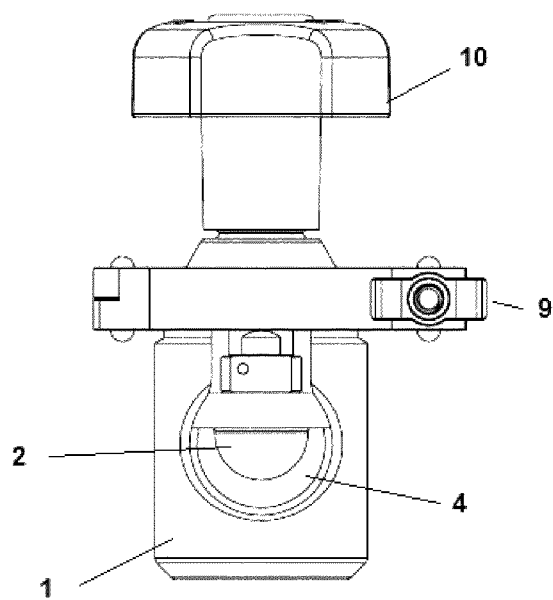
Figure 3a
Figure 3b

PINCH VALVE

FIELD OF THE INVENTION

This invention relates to a pinch valve assembly. In particular, a pinch valve assembly for use with polymeric single use technologies in the bioprocessing industry, and for compression of polymeric tubing in general.

BACKGROUND

Bioprocessing involves the use of living cells or components to create products and compounds. Isolation of the living cells or components within a given process is of the utmost importance as contamination can render products unsuitable for use. To reduce the risk of contamination in the bioprocessing industry, many components are "single use". Within the industry, "single-use" technologies refer primarily to polymeric components—such as tubing and bags. These components are used to house and transport cell culture medias for a single batch of product only. After use, the components are removed from production use and replacement components are used for the next production batch.

The intention of "single use" components is to protect the media from cross-contamination with alternative production batches, to eliminate the requirement for sterilisation and cleaning/sanitisation of process equipment, and to prevent bacterial contamination.

Tubing is used throughout bioprocessing to transport media from one process point to another, e.g. from one machine to another in a given processing plant. Tubing is often required to be sealed, for example to stop the flow of a given media through a tube and to prevent further transfer of media from one point to another in a process. This tubing is frequently single use and fabricated from polymeric materials. Components used to seal the tubing is also frequently single use and again made from polymeric materials. As such, the tubing and sealing arrangement is typically single use—the tubing and sealing components are not used beyond one production batch of a given bio product.

Single-use polymeric devices are not durable devices, and are generally rated for use with one production batch only. They are not designed to provide a reusable assembly. In addition, little or no control can be provided to achieve a desired flow rate for transfer of media.

Hybrid options are available which can allow for more than a single use. These often rely on a stainless steel valve construction which is reusable for 'pinching' of a molded polymer tube.

Such hybrid stainless-steel assemblies are more durable than a complete single use valve and tubing arrangement. Hybrid assemblies allow for re-use from batch-to-batch once new tubing is used as the product contact material. However, the significant number of single use tubing sizes—determined by the tubing inner diameter—and differing tubing wall thickness available to the market, render stainless-steel valve assemblies for all single-use tubing sizes impractical and cost inefficient for both equipment manufacturer and end user.

A pinch valve assembly that can be re-used on existing single-use tubing, ensuring no possibility of contamination to a production batch would be an improvement on the state of the art.

SUMMARY OF THE INVENTION

An embodiment of the present invention includes a pinch valve assembly for compression of a fluid conduit comprising: an assembly housing; an interchangeable compressor element; an interchangeable holder element for holding a fluid conduit, the holder element facing the interchangeable compressor element; the valve assembly being configured such that the compressor element is moveable towards the holder element within the assembly housing for compression of a fluid conduit between the compressor and the holder elements.

This is advantageous as the both the compressor and the holder element may be easily removed and replaced as required by a user. Holder elements can be dimensioned to be suitable for use with different sizes of fluid conduit. This means that the holder may be selected to most suitably fit a given fluid conduit size but the need to remove or replace the entire valve assembly, if for example a different conduit size is required, is obviated. Furthermore, the holder may be a single use element while the overall valve assembly may be suitable for multiple uses. In addition, using interchangeable holders and compressors, the end user can adapt the valve internals to suit multiple fluid conduit diameters and conduit wall thickness—without the requirement to use an entire new valve assembly. An interchangeable compressor element and an interchangeable holder element provides that the assembly is customisable by the end user. This provides a significant advantage as components of the assembly are interchangeable after installation, without structurally altering the overall pinch valve assembly valve or affecting a product stream. Furthermore, the interchangeable components are simple to install and interchange and can be done by an end user, contractor or equipment maker.

In use, the compressor element of the valve assembly may be moveable between an open position wherein a fluid conduit between the compressor and the holder elements is uncompressed and a closed position wherein a fluid conduit between the compressor and the holder elements is compressed. This is advantageous as the assembly thus provides for compression, and as a result, closing of a fluid conduit which is positioned between the compressor and holder elements. This provides for effective termination of flow of media through the conduit when the compressor element is in the closed position. The conduit may be subsequently uncompressed, and as a result opened, to allow flow of media through the conduit to recommence if required.

The holder element may comprise a threaded channel in a base portion. The holder element may be fixable to the assembly housing via a threaded bolt inserted into the threaded channel of the base portion. This is advantageous as it provides an easy to use means of securing the holder element to the base portion. This is advantageous as it provides that the interchangeable holder element may be easily and quickly removed and replaced as required.

The valve assembly may further comprise a closure assembly fixable to the valve assembly housing. This is advantageous as it provides a means to operate the valve assembly.

The closure assembly may be fixed to the valve assembly housing with a clamp. This is advantageous as it provides an easy to use means of securing the valve assembly and the closure assembly together. The clamp may be easily opened for separation of the valve assembly and closure assembly, for example for replacement of the closure assembly and furthermore, the clamp may be readily re-closed once the desired closure and valve assemblies are in place.

The closure assembly may be configured to be manually actuated. The closure assembly may comprise an elongate element wherein the closure assembly is configured to move the compressor element from the open position to the closed position by application of a twisting force to the elongate element.

This is advantageous as it provides for a manner of user control over the opening and closing of the closure assembly and thus provides for user control over the valve assembly itself.

The closure assembly may be configured to be pneumatically actuated. The closure assembly may comprise a biased element wherein the closure assembly is configured to move the compressor element from the open position to the closed position by pneumatic actuation of the biased element.

This is advantageous as it provides for rapid switching between the open position and closed position of the compressor element. It further provides a safeguard against failure of the value assembly as the pneumatic actuation can provide for the valve assembly to fail into an open position or a closed position, whichever is deemed most appropriate for a given process.

The compressor of the valve assembly may be fabricated from stainless steel. This is advantageous as it provides for a very durable assembly suitable for more than a single use. The holder of the valve assembly may be fabricated from Polyphenylsulfone, PPSU. This is advantageous as PPSU components may be easily fabricated in a variety of shapes to suit many fluid conduit shapes and profiles.

The fluid conduit may be a polymeric tube. Such tubes are typical in the bioprocessing industry. Thus, use of such a tube as a fluid conduit provides that the valve assembly is particularly suited for use in the bioprocessing industry.

DESCRIPTION OF FIGURES

FIG. 3a is a cut away representation of the pinch valve assembly of the invention coupled to a manually operated closure assembly with the compressor element in the closed position FIG. 3b is a representation of the pinch valve assembly of the invention coupled to a manually operated closure assembly with the compressor element in the closed position

DETAILED DESCRIPTION

Figure 1:
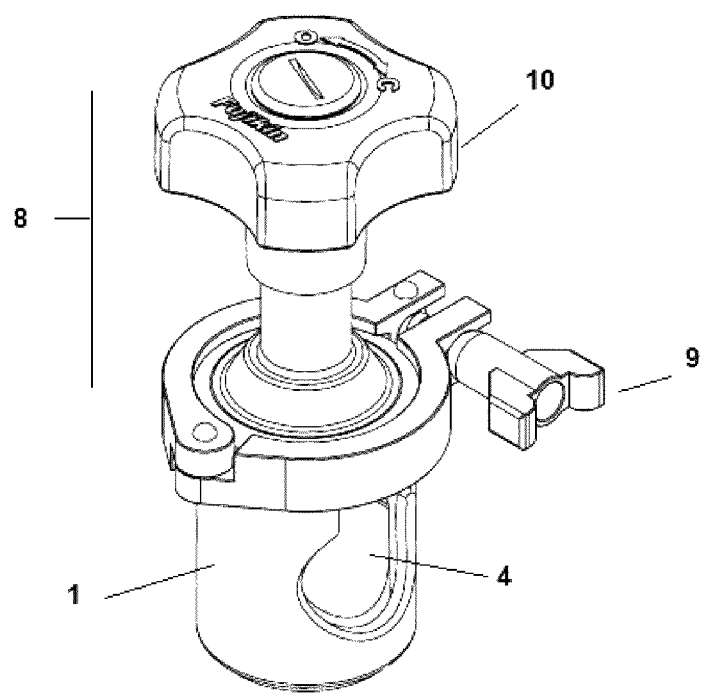
FIG. 1 is a representation of the pinch valve assembly of the invention coupled to a manually operated closure assembly
Figure 2A:
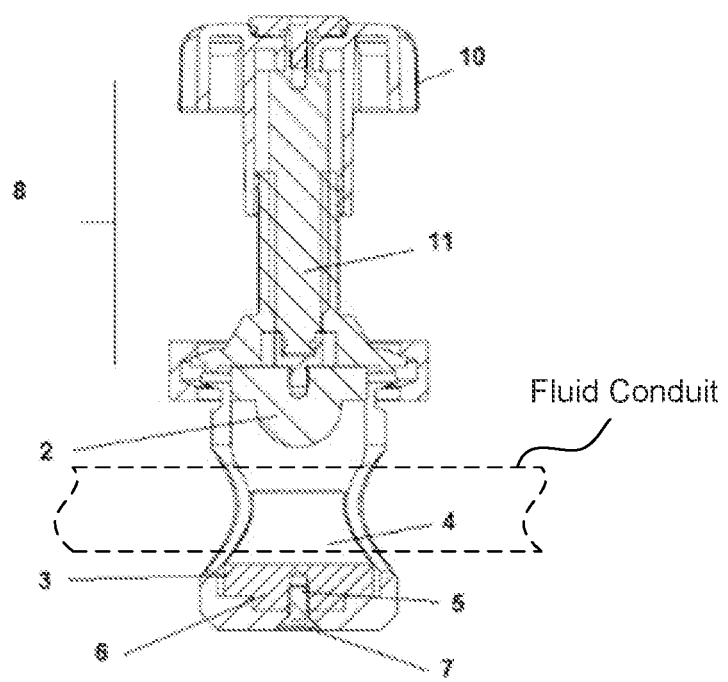
FIG. 2a is a cut away representation of the pinch valve assembly of the invention coupled to a manually operated closure assembly with the compressor element in the open position
Figure 2B:
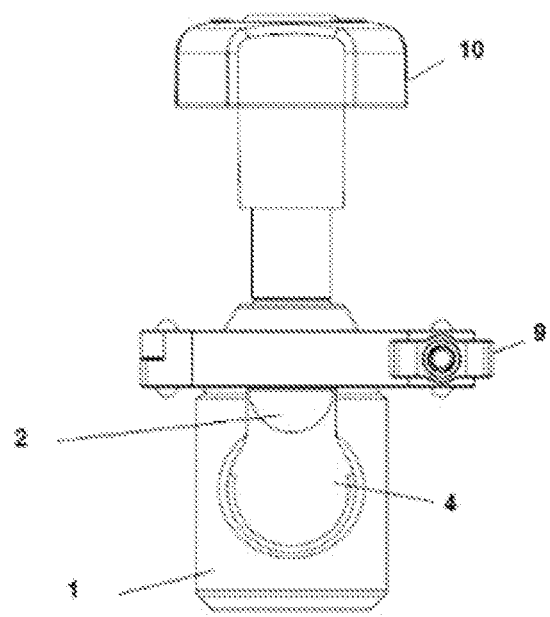
FIG. 2b is a representation of the pinch valve assembly of the invention coupled to a manually operated closure assembly with the compressor element in the open position

The invention will now be described with reference to the accompanying figures.

FIGS. 1 to 6 show the pinch valve assembly of the invention for compression of a fluid conduit. The pinch valve assembly comprises an assembly housing 1; an interchangeable compressor 2; an interchangeable holder 3 for holding a fluid conduit, the holder 3 is positioned facing the interchangeable compressor 2.

The pinch valve assembly is configured such that the compressor 2 is moveable towards the holder 3 within the assembly housing 1 for compression of a fluid conduit which can be placed in an opening 4 in the housing 1 between the compressor 2 and the holder 3.

The compressor 2 is moveable between an open position (Seen in FIGS. 2a and 2b, 5a and 5b) wherein a fluid conduit (not shown) placed in the opening 4 between the compressor 2 and the holder 3 is uncompressed and a closed position (Seen in FIGS. 3a and 3b, 6a and 6b) wherein a fluid conduit placed in the opening 4 between the compressor 2 and the holder 3 is compressed by the action of the compressor 2 being moved towards the holder 3. When the fluid conduit, for example a tube, is made from a deformable material, for example rubber tubing or other polymeric tubing, compressing the conduit has the effect of "pinching" and thus closing the fluid conduit. The conduit may be uncompressed by movement of the compressor 2 back to the open position.

Within the housing, the interchangeable holder 3 may be selected to best match the profile of the tubing to be used for a given bioprocess being undertaken. The holder 3 comprises a threaded channel 5 in a base portion 6. The holder 3 is secured to the housing using a threaded bolt 7 which has the effect of fixing the holder in place within the housing. Different holders may be used as necessary depending on the tubing required, without any requirement to change the housing 1 or the closure assembly 8, 15.

The closure assembly 8, 15 may be secured to the housing 1 through mating ferrule ends and the closure assembly 8, 15 and housing 1 are clamped together using a triclamp 9.

The interchangeable compressor 2 is configured to match the profile of the tubing to be used for the process. The compressor 2 is secured to a stem 11, 17 structure of the closure assembly through mating threads. A threaded channel is provided in the compressor 2 into which a threaded end of the stem 11, 17 may be secured. Both the stem 11, 17 and the compressor 2 may be provided with a suitable coating to prevent seizing. This provides that no lubricants which could come into contact with the operator are required to be used in the overall assembly.

The compressor 2 and the housing 1 of the pinch valve assembly may be comprised of stainless-steel to provide sufficient strength and durability to the valve. The holder 3 of the pinch valve assembly may be comprised of Polyphenylsulfone, PPSU.

Figure 4:
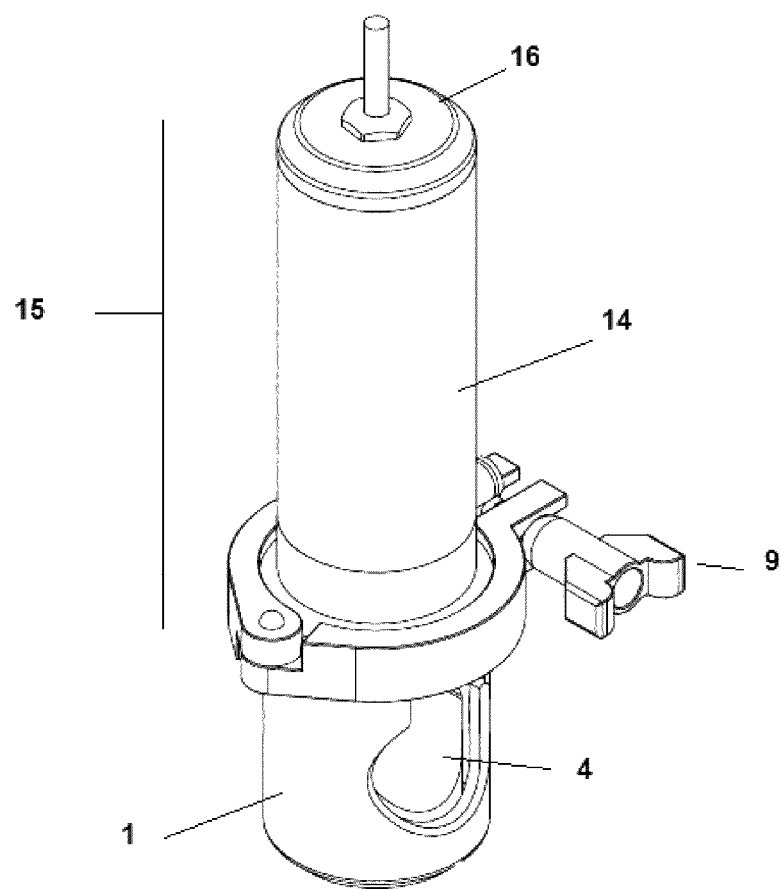
FIG. 4 is a representation of the pinch valve assembly of the invention coupled to a pneumatically operated closure assembly
Figure 5A:
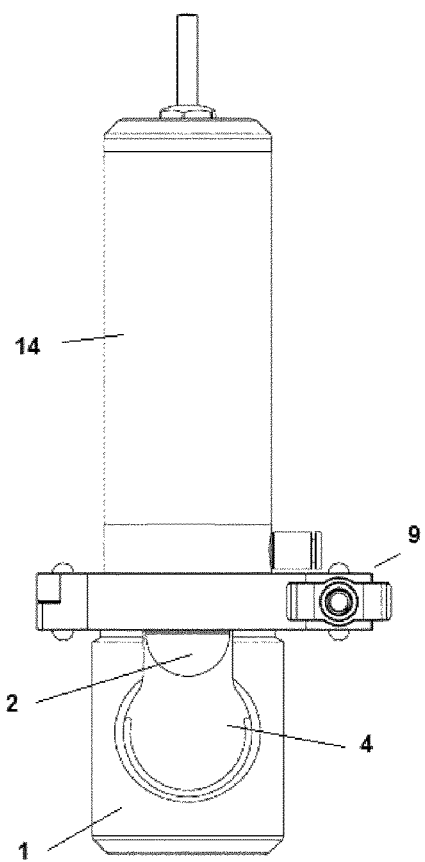
FIG. 5a is a representation of the pinch valve assembly of the invention coupled to a pneumatically operated closure assembly with the compressor element in the open position
Figure 5B:
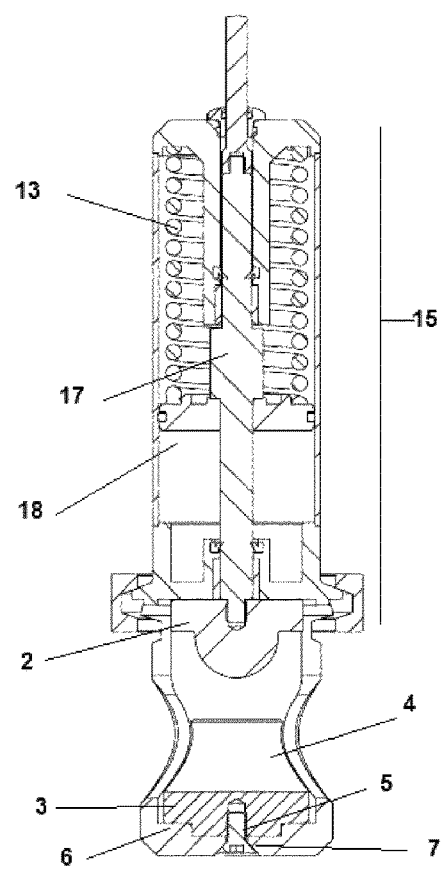
FIG. 5b is a cut away representation of the pinch valve assembly of the invention coupled to a pneumatically operated closure assembly with the compressor element in the open position
Figure 6A:
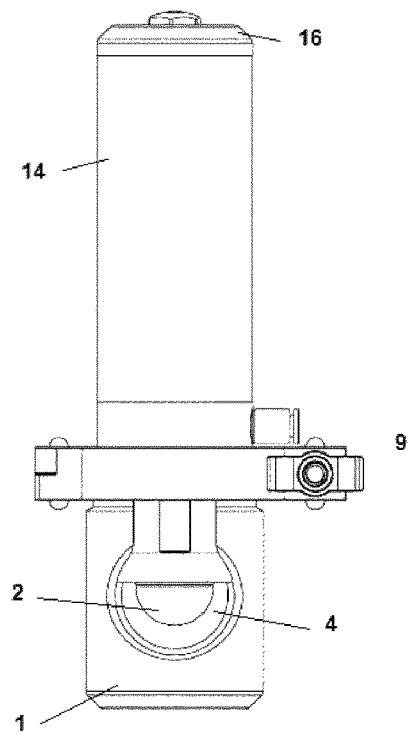
FIG. 6a is a representation of the pinch valve assembly of the invention coupled to a pneumatically operated closure assembly with the compressor element in the closed position
Figure 6B:
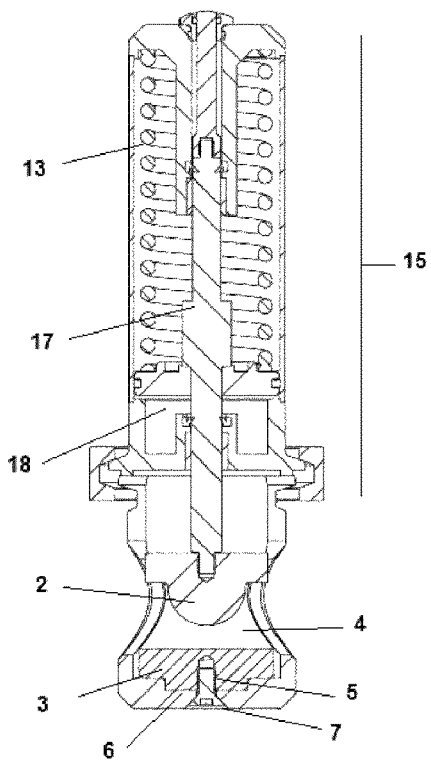
FIG. 6b is a cut away representation of the pinch valve assembly of the invention coupled to a pneumatically operated closure assembly with the compressor element in the closed position

The pinch valve assembly can be provided with a manual closure assembly 8 (FIGS. 1, 2 and 3) or pneumatic closure assembly 15 (FIGS. 4, 5 and 6).

The manual closure assembly 8 comprises an elongate element or stem 11 and the closure assembly is configured to move the compressor 2 from the open position to the closed position and vice versa, by application of a torque or twisting force by a user to the stem 11 via a cap or bonnet 10. In an embodiment of the invention, there is provided a manual PV compressor holder attached to the stem. This provides the function of removing twisting motion from the stem and provides that a linear motion moves the compressor 2 from the open position to the closed position and vice versa.

The manual closure assembly 8 comprises a coated bonnet 10 and an actuator housing. The bonnet 10 may be manufactured from stainless-steel. The bonnet 10 is threaded to match a suitably-coated stem 11. The stem 11 may be manufactured from stainless-steel. The bonnet and stem are dimensioned and configured to produce the required linear force and stroke to compress and seal the fluid conduit in use. The closure assembly 8 is configured to produce a force to ensure a leak integrity to meet ANSI FCI 70/2 Class VI specification. The stroke of the stem 8 is configured to ensure the fluid conduit in use returns to an uncompressed state (i.e. fully open) when the closure assembly 8 is actuated by twisting to the open position. A polymer PPS (40% GF) is utilised to ensure a light-weight assembly for a manual hand wheel for twisting between the open and closed positions.

The pneumatic closure assembly 15 comprises a biased element in the form of a spring element 13 fixed to a stem 17 and the closure assembly is configured to move the compressor 2 from the open position to the closed position by pneumatic actuation of the biased element.

The pneumatic closure assembly 15 utilises a suitably-coated compressor head 16. The compressor head 16 may be manufactured from stainless-steel. The compressor head 16 is threaded to match a stem 17. The stem 17 may be manufactured from stainless-steel. The bonnet and stem are dimensioned and configured to produce the required linear force and stroke to compress and seal the fluid conduit in use. The closure assembly 15 is configured to produce a force to ensure a leak integrity to meet ANSI FCI 70/2 Class VI specification.

A spring element 13 provides a biased force to the stem 17. Again, the stroke of the stem 8 is configured to ensure the fluid conduit in use returns to an uncompressed state (i.e. fully open) when the closure assembly 15 is actuated to the open position. A thin-wall actuator housing 14 may be utilised to ensure a light-weight assembly. A suitable biased force for the spring element 13 may be selected to provide a default position for the valve assembly—i.e. fail-open, fail-closed or fail-freeze. In FIG. 6, a fail-closed type is illustrated. An air-tight piston 18 allows pneumatic control of the closure assembly 17 to achieve the required "pinching" functionality.

The present invention provides for the possibility to change between manual and pneumatic closure modes. To do so, for example a manual closure assembly 8 may be removed by releasing the triclamp 9 and a pneumatic closure assembly 15 may be attached by re-sealing the self-same triclamp 9 to fix the closure assembly 15 to the pinch valve assembly.

To change between tubing sizes, the interchangeable holder 3 and compressor 2 may be removed and replaced. Each compressor 2 and holder 3 may be configured to ensure the same closure assembly 8 and valve body will provide the required stroke to impinge on the fluid conduit to the required depth and force to seal the conduit against internal fluid pressure—without damage to the conduit structure. In an embodiment of the invention, the compressor element 2 may be provided in the closure assembly such that removal and replacement of the closure assembly further results in removal and replacement of the compressor element 2.

Existing metallic pinch valve structures can be used for one process line (i.e. tube or conduit) size only, requiring separate valve assemblies for each single-use line size. The present invention provides that interchanging of the holder 2 and compressor 3 is the only requirement to change between line sizes within a specified size range.

The words "comprises/comprising" and the words "having/including" when used herein with reference to the present invention are used to specify the presence of stated features, integers, steps or components but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The invention claimed is:

1. A pinch valve assembly for compression of a fluid conduit comprising:
   an assembly housing;
   an interchangeable compressor element, the interchangeable compressor element comprising a first threaded channel for fixing to a threaded end of a stem of a closure assembly;
   one interchangeable holder element dimensioned for holding the fluid conduit, the holder element facing the interchangeable compressor element, wherein the holder element further comprises a second threaded channel in a base portion for fixing the holder element within the assembly housing via a threaded bolt inserted into the second threaded channel; and
   the valve assembly being configured such that, in use, the compressor element is moveable by the closure assembly towards the holder element within the assembly housing for compression of the fluid conduit between the compressor element and the holder element,
   wherein the assembly housing includes a first stepped surface formed along an inner surface of the assembly housing, and the base portion includes a second stepped surface formed on an outer surface of the base portion, the second stepped surface engaging the first stepped surface of the assembly housing.

2. The pinch valve assembly of claim 1 wherein, in use, the compressor element is moveable between an open position wherein the fluid conduit between the compressor element and the holder elements is uncompressed and a closed position wherein the fluid conduit between the compressor and the holder elements is compressed.

3. The pinch valve assembly of claim 1 further comprising the closure assembly fixable to the assembly housing.

4. The pinch valve assembly of claim 3 wherein the closure assembly is configured to be manually actuated.

5. The pinch valve assembly of claim 4 wherein the closure assembly comprises an elongate element and wherein the closure assembly is configured to move the compressor element from the open position to the closed positon by application of a twisting force to the elongate element.

6. The pinch valve assembly of claim 3 wherein the closure assembly is configured to be pneumatically actuated.

7. The pinch valve assembly of claim 6 wherein the closure assembly comprises a biased element and wherein the closure assembly is configured to move the compressor element from the open position to the closed positon by pneumatic actuation of the biased element.

8. The pinch valve assembly of claim 1 wherein the compressor element is fabricated from stainless steel.

9. The pinch valve assembly of claim 1 wherein the holder element is fabricated from Polyphenylsulfone, PPSU.

10. The pinch valve assembly of claim 1 wherein the fluid conduit is a polymeric tube.

11. A pinch valve assembly for compression of a fluid conduit comprising:
- an assembly housing;
- an interchangeable compressor element, the interchangeable compressor element comprising a first threaded channel for fixing to a threaded end of a stem of a closure assembly;
- one interchangeable holder element dimensioned for holding a fluid conduit, the holder element facing the interchangeable compressor element, wherein the holder element further comprises a second threaded channel in a base portion for fixing the holder element within the assembly housing via a threaded bolt inserted into the second threaded channel; and
- the valve assembly being configured such that, in use, the compressor element is moveable by the closure assembly towards the holder element within the assembly housing for compression of the fluid conduit between the compressor element and the holder element, wherein the closure assembly is selectively fixed to the assembly housing with a clamp, the assembly housing being detachable from the closure assembly and the compressor element by changing a clamping force of the clamp, and
- wherein the assembly housing includes a first stepped surface formed along an inner surface of the assembly housing, and the base portion includes a second stepped surface formed on an outer surface of the base portion, the second stepped surface engaging the first stepped surface of the assembly housing.

* * * * *